Sept. 2, 1947. R. C. BOWMAN Plant Pat. 757

PEAR TREE

Filed March 21, 1946

Inventor

ROY C. BOWMAN

By Francis J. Klempay

Attorney

Patented Sept. 2, 1947

Plant Pat. 757

UNITED STATES PATENT OFFICE

757

PEAR TREE

Roy C. Bowman, Youngstown, Ohio

Application March 21, 1946, Serial No. 656,044

1 Claim. (Cl. 47—62)

My invention and discovery relates to improvements in pear trees of a variety useful in a practical sense, in the production of the beneficial and succulent pear fruit. These improvements, which are of varying nature and importance, are the result of some twenty-five years' study and experimentation in the horticulture of this fruit, and arose primarily, I believe, from a cross-pollination of the Keefer and Anjou varieties. The resultant original seedling has been asexually reproduced by cutting and grafting. It was and is my object to improve both the tree and the fruit particularly as regards the health and bearing consistency of the former and the keeping qualities of the latter. Notwithstanding the clear desirability of imparting better keeping characteristics to the pear fruit, particularly since the keeping qualities of this fruit are now generally unreliable, little progress has heretofore been made in this regard. I have now definitely established that the improved variety of pear tree developed by me consistently produces fruit which will, under the same conditions of storage, remain in wholesome, edible condition substantially longer than any other pear fruit of which I am aware.

Figure 1:
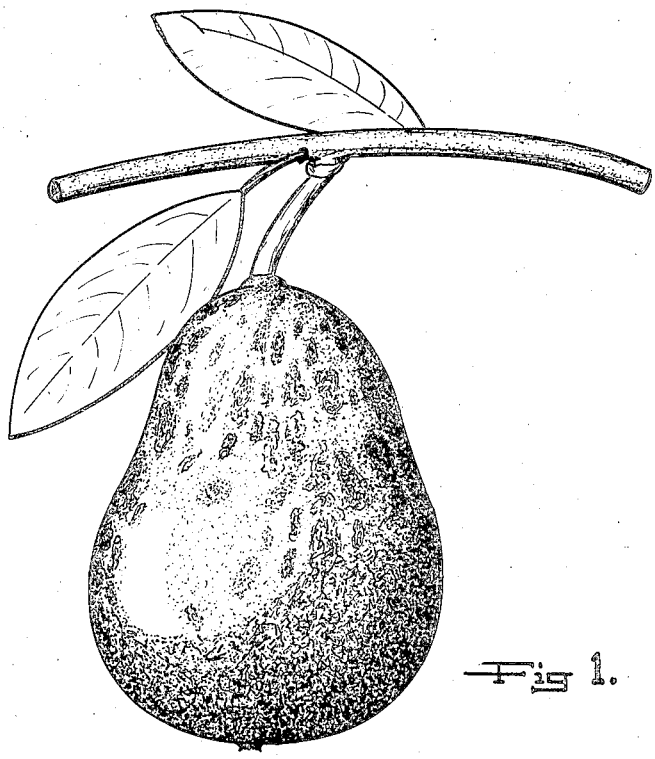
Figure 2:
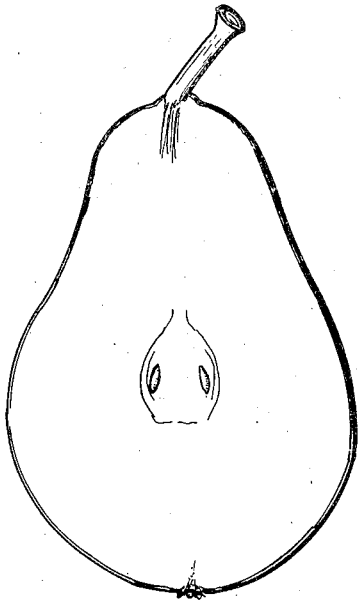

The following description and the accompanying illustrations disclose in detail the distinguishing characteristics of my improved pear tree and of the fruit of such tree. In the drawing, Figure 1 is a side view of the fruit of my improved tree and of a portion of the wood and leaves of this tree while Figure 2 is a sectional view of the fruit showing the core and seeds.

The tree is characterized particularly by its hardiness and by its long and slim limbs which are quite supple, flexible and strong and so capable of carrying heavy yields without breakage. There is a pronounced tendency for both the foliage and the fruit to concentrate near the outer ends of the branches, the fruit being more or less clustered only slightly inwardly from the outer ends of the branches. The bark is smooth and firm, reflecting the health and vigor of the plant, and this general characteristic is also apparent in the deep green glossy leaf which has greater permanency than the leaf of any other variety of pear tree of which I am aware—retaining its green color and remaining on the tree until quite late in the fall.

An outstanding characteristic of the tree of my invention is its prolonged and double blossoming period. Altogether the full blossoming time consumes approximately four weeks divided into two consistent and readily discernible periods or cycles—the first profusion remaining approximately ten days and then approximately two weeks after the opening of the first blossoms the second blossoming sets in. The second blossoming is somewhat less profuse than the first but is substantially of equal durability. This double blossoming period has proven itself beneficial as regards consistency of bearing at least insofar as propagation in the northeastern Ohio region is concerned where late frosts are not uncommon. No distinguishing characteristics of the blossoms per se have been observed.

The tree described herein is further characterized by its apparent freedom from suckering and by its greater resistance to blight, these characteristics being deduced from closely observing the growth of the wood and comparing over a period of nine years, such growth as well as the general well being of a number of the trees with the growth and well being of other varieties. These observations as well as accelerated propagations of the wood have demonstrated that the plant is readily reproducible and is definitely non-reversionary in character. In the grafting operations the best results have been obtained by the use of apple seedlings as the base stock.

The fruit of the pear tree of my invention is characterized particularly by its measurably improved keeping qualities. The fruit is hard and firm when plucked from the tree about October 1st in the northeastern Ohio region and when stored under average conditions will remain firm and succulent into the following March. The flesh is very juicy and very sweet even at picking time and is similar in flavor to the Anjou pear. It is believed that the good keeping quality results from the firm, impervious and permanent nature of the skin of the fruit, the outer surface of which is mottled and rustic substantially as illustrated. In color, the surface is a light pastel green mottled with light brown and there is a pronounced tendency to a bright red cheek.

In shape, the fruit is similar to the Bartlett pear but the lobe or region of maximum diameter is somewhat higher up along the vertical axis of the fruit. In this respect the shape is similar to the Anjou pear but the present variety is readily distinguishable from the Anjou pear in its smaller size, and different surface texture and coloring. The fruit is further characterized by its very faint core and few seeds, the seeds being clustered in a small area about one third up the core of the fruit.

Another definite distinguishing mark of the fruit is the healthy, vigorous, thick and permanent character of the stem. As shown, the stem is stocky and has a pronounced tendency to overgrow the nib of the supporting branch while the flesh of the fruit overgrows the lower portion of the stem. The stem is always angularly related to the axis of the core of the fruit.

I claim:

The new and distinct variety of pear tree herein described characterized particularly by its double blossoming period, its long slim tough limbs, its apparent freedom from suckering and blight; by the superior keeping qualities of its fruit, the faint core and few seeds of the fruit; and by the vigorous, thick and permanent nature of its fruit stems.

ROY C. BOWMAN.